(12) United States Patent
Nara et al.

(10) Patent No.: US 10,407,710 B2
(45) Date of Patent: Sep. 10, 2019

(54) DISPOSABLE TEST STRIP DEVICE FOR ANALYTE DETECTION IN A BODY LIQUID SAMPLE

(71) Applicant: GOODWILLER OY, Oulu (FI)

(72) Inventors: Petteri Nara, Oulu (FI); Petri Sarkela, Kempele (FI); Teemu Makiniemi, Oulu (FI)

(73) Assignee: GOODWILLER OY, Oulu (FI)

( * ) Notice: Subject to any disclaimer, the term of this patent is extended or adjusted under 35 U.S.C. 154(b) by 339 days.

(21) Appl. No.: 14/554,398

(22) Filed: Nov. 26, 2014

(65) Prior Publication Data

US 2015/0152468 A1 Jun. 4, 2015

(30) Foreign Application Priority Data

Dec. 3, 2013 (FI) .................................... 20136208

(51) Int. Cl.

| | |
|---|---|
| *C12Q 1/32* | (2006.01) |
| *G01N 33/52* | (2006.01) |
| *C12Q 1/26* | (2006.01) |
| *G01N 33/98* | (2006.01) |

(52) U.S. Cl.
CPC .............. *C12Q 1/32* (2013.01); *C12Q 1/26* (2013.01); *G01N 33/523* (2013.01); *G01N 33/525* (2013.01); *G01N 33/526* (2013.01); *G01N 33/98* (2013.01)

(58) Field of Classification Search
CPC . C12Q 1/32; C12Q 1/26; G01N 33/98; G01N 33/523; G01N 33/525; G01N 33/526
See application file for complete search history.

(56) References Cited

U.S. PATENT DOCUMENTS

| | | | |
|---|---|---|---|
| 4,734,360 A | 3/1988 | Phillips | |
| 4,786,596 A | 11/1988 | Adams | |
| 4,810,633 A | 3/1989 | Bauer et al. | |
| 4,900,666 A | 2/1990 | Phillips | |
| 4,962,025 A | 10/1990 | Moldowan | |
| 5,268,146 A | 12/1993 | Lawrence et al. | |
| 6,485,983 B1 * | 11/2002 | Lu ....................... | G01N 33/558 204/288 |
| 6,673,630 B2 | 1/2004 | Albarella et al. | |
| 7,049,130 B2 * | 5/2006 | Carroll ................. | G01N 33/525 422/408 |
| 7,378,285 B2 * | 5/2008 | Lambotte ......... | G01N 33/54366 422/412 |
| 7,387,890 B2 * | 6/2008 | Esfandiari ............ | G01N 33/558 422/422 |
| 7,521,259 B2 * | 4/2009 | Petruno .............. | G01N 21/8483 422/504 |
| 7,521,260 B2 * | 4/2009 | Petruno .............. | G01N 21/8483 422/402 |
| 7,560,288 B2 * | 7/2009 | Carroll ................. | G01N 33/525 422/408 |
| 7,704,753 B2 * | 4/2010 | Tang .................... | G01N 33/558 422/402 |
| 7,785,899 B2 * | 8/2010 | Saul .................... | G01N 33/558 435/287.1 |
| 8,470,608 B2 * | 6/2013 | Babu ................... | G01N 33/558 422/401 |
| 2002/0031840 A1 | 3/2002 | Albarella et al. | |
| 2006/0024835 A1 | 2/2006 | Matzinger et al. | |
| 2008/0220462 A1 * | 9/2008 | Bell ........................ | C12Q 1/37 435/15 |
| 2013/0040289 A1 * | 2/2013 | Jumonville .............. | C12Q 1/28 435/5 |

FOREIGN PATENT DOCUMENTS

| | | |
|---|---|---|
| EP | 0117032 | 8/1984 |
| EP | 1130395 | 9/2001 |
| EP | 1 359 417 A2 | 11/2003 |
| EP | 1621887 | 2/2006 |
| WO | 9957562 | 11/1999 |
| WO | 0017636 | 3/2000 |

OTHER PUBLICATIONS

Finnish Search Report dated Jul. 11, 2014, corresponding to the Foreign Priority Application No. 20136208.
European Search Report dated Apr. 2, 2015, corresponding to the European Priority Application No. 14195044.4.

* cited by examiner

*Primary Examiner* — Aaron J Kosar
(74) *Attorney, Agent, or Firm* — Young & Thompson

(57) ABSTRACT

A disposable, enzymatic assay based test strip device for colorimetric detection of an analyte compound, such as ethanol, in a body liquid sample, such as saliva, is provided. The test strip device includes at least one reactive test zone configured to develop a visual indication when the concentration of the analyte compound in the body liquid sample exceeds a predetermined limit, and a reactive control zone configured to develop a visual indication upon being supplied with the body liquid sample. The test strip device further includes a compound buffer, preferably selected from non-volatile alcohols and disposed to closely adjoin the reactive control zone such, that the content of the compound buffer admixes with the reagents provided within the reactive control zone, while the control zone is being supplied with the body liquid sample. Deposition of the reactive zones is preferably implemented by conventional printing methods utilizing biological inks.

22 Claims, 7 Drawing Sheets

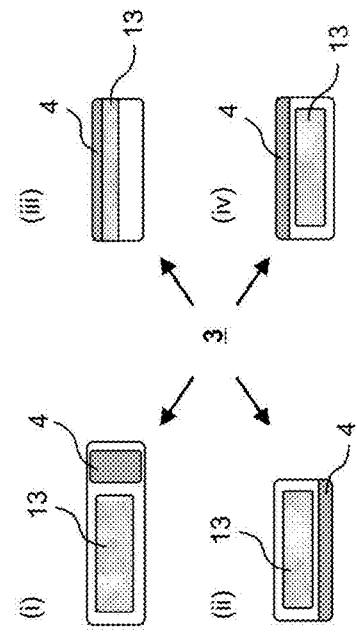
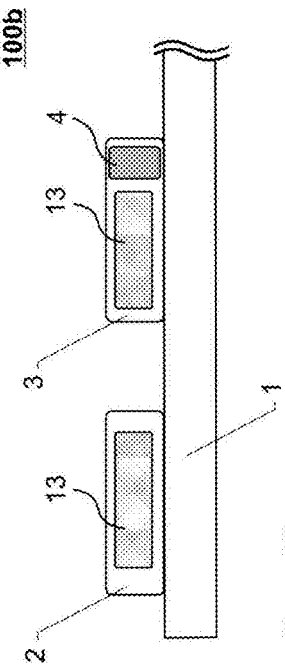
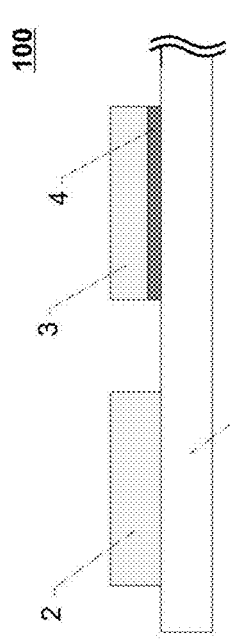
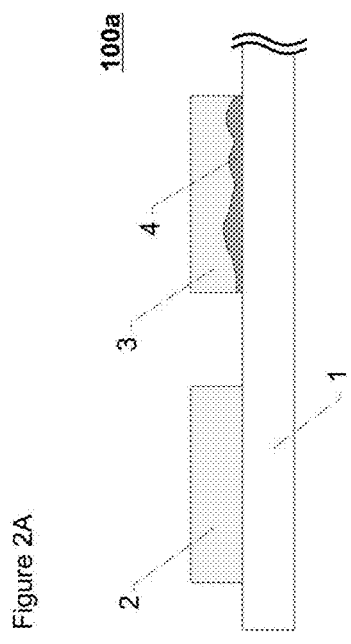
Figure 2A
Figure 2B
Figure 2C
Figure 2D
Figure 2E

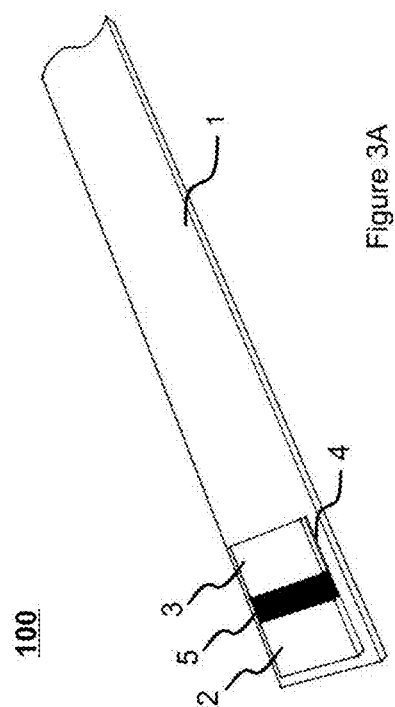
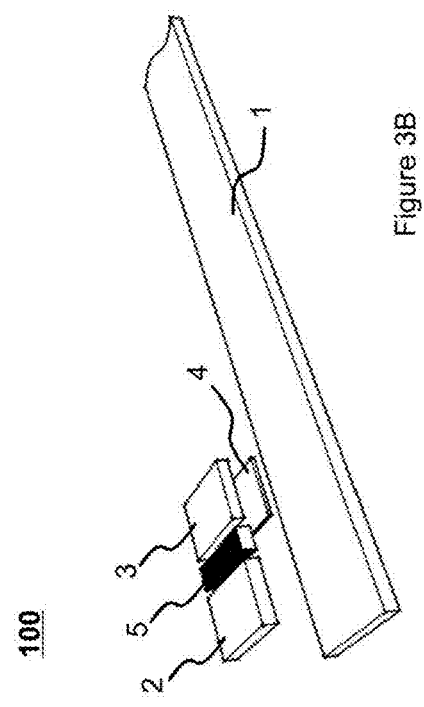
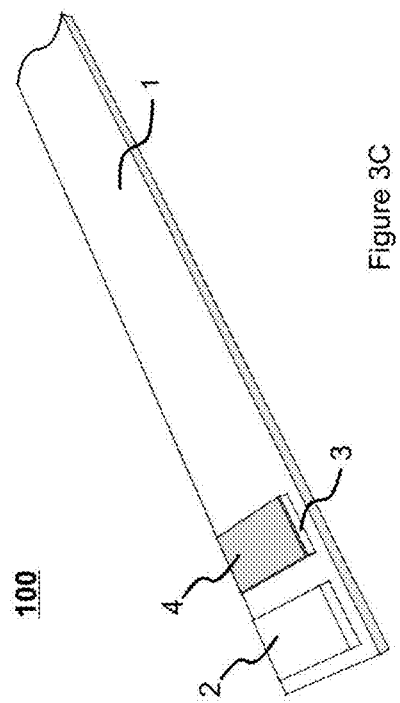
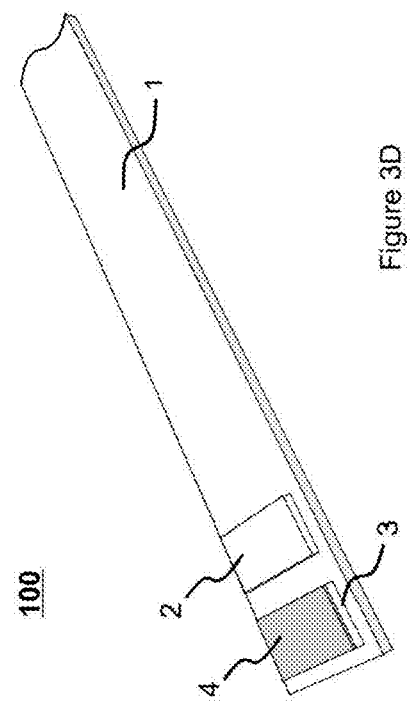

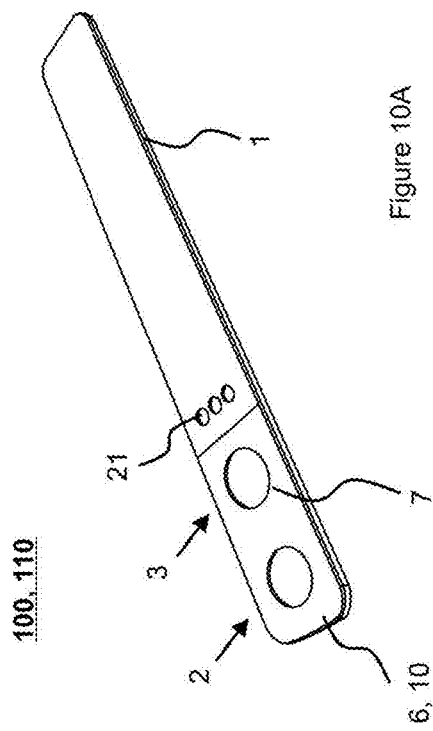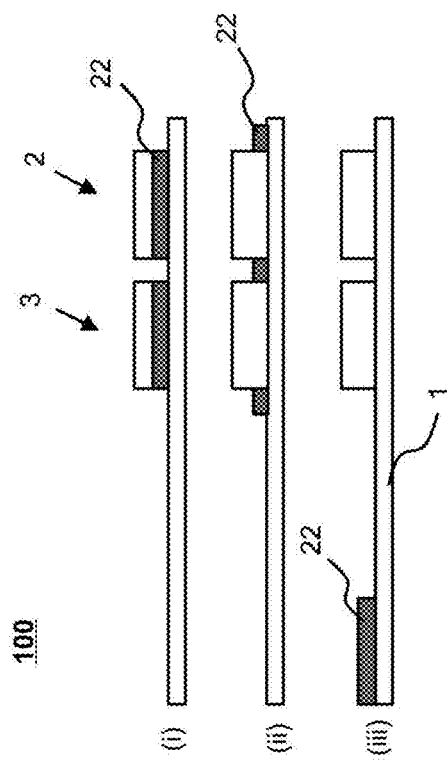
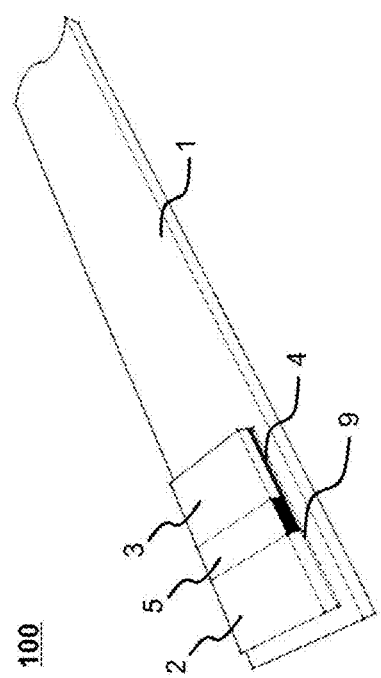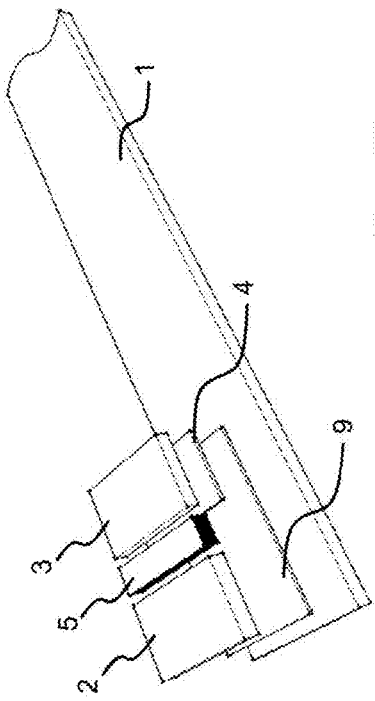

DISPOSABLE TEST STRIP DEVICE FOR ANALYTE DETECTION IN A BODY LIQUID SAMPLE

FIELD OF THE INVENTION

The invention generally relates to disposable test strip devices for detection of analytes in body liquid samples. In particular, the present invention concerns a disposable, enzymatic assay based test strip device for semi-quantitative colorimetric detection of alcohol in a body liquid sample, such as saliva.

BACKGROUND

Utilization of disposable test strip devices represents the most simple, fast and convenient technique for determination of a variety of analytes in body liquid samples, such as blood, plasma, serum, urine and saliva. For detecting analytes in body liquid samples by disposable test strips two major approaches are generally utilized. The first approach is immunochemical; antibody-antigen interaction based test strips comprise, in addition to an actual detection zone, also a control zone Immune assay based tests are historically rendered for hormone detection from blood or urine; manufacturing thereof is rather expensive, so as the final product, correspondingly.

The second major approach originates from enzymatic assays for colorimetric detection, wherein the presence of analyte in biological sample is determined qualitatively and/or semi-quantitavely by observing color changes within a detection portion of a test strip. Disposable analytic test strip devices for determination of analyte, such as ethanol, in human body liquid samples, such as whole blood, serum, saliva or urine, by means of colorimetric, alcohol oxidase based reaction are disclosed in U.S. Pat. No. 4,734,360 (Philips), U.S. Pat. No. 4,786,596 (Adams) and U.S. Pat. No. 4,810,633 (Bauer and Magers). Those test strip devices generally comprise the enzymes alcohol oxidase and peroxidase, along with a chromogenic indicator system incorporated into a carrier matrix. Alcohol oxidase functions as a catalyst to convert ethanol present along with ambient oxygen in a liquid sample to acetaldehyde and hydrogen peroxide. Peroxidase, in turn, functions as a catalyst to induce a color change in the hydrogen donor and convert the hydrogen peroxide to water. Determination of analyte levels in the sample is performed by visual estimation of shade and intensity of color developed in the detection area. Visual estimation can be performed qualitatively by observing color development in an otherwise blank detection area, as disclosed in e.g. U.S. Pat. No. 4,734,360, or semi-quantitavely, by visually comparing a tone and an intensity of the colored detection area to a printed standard/color map, as disclosed in U.S. Pat. No. 4,962,025 (Moldowan), for example. In opposite to immunochemical test strips, aforementioned enzymatic colorimetric solutions are not provided with a separate control area, whose purpose is to confirm that the test had worked correctly. Therefore, a common drawback of such tests is their rather low reliability, resulting in a high number of fault results. Disposable test strip devices comprising a distinct control area are also known. Thus, European patent No. 1,130,395 (Albarella et al) discloses a colorimetric test strip for detecting the absence or presence of glucose in urine, which test strip comprises, in addition to detection ("reagent") areas, one or more reference color areas with predetermined color shades that are different from the color shades of said reagent areas prior to use. Said reference color areas are originally manufactured to comprise a predetermined color, so that the purpose thereof is to facilitate the comparison between the detection- and the reference zones. Mentioned reference color area(s) does not involve any reactive chemistry.

A test strip device, disclosed in European patent No. 1,621,887 (Matzinger et al), comprises a matrix having sample detection- and a control zones, provided with a first—and a second reagent composition, respectively. The test strip is, however, rendered for detection of glucose in blood samples and requires a measuring device, such as a reflectometer, for reading test results.

Mentioned prior art devices and related methods for detection of an analyte compound, such as alcohol, in a biological sample, are therefore hindered with several drawbacks, such as lack of reliability caused by the absence of an opportunity to perform control reaction and, therefore, increased possibility of obtaining fault results and/or misinterpretation of the results obtained. From the other hand, those test strip devices, that in one way or another are provided with the control zone, are typically rendered to detect other analytes than alcohol from such biological samples, whose collection is rather problematic, provided as impossibility therefor to be collected "on-the-go" and/or requirements for performing invasive actions.

Amidst body liquid samples collectable in a non-invasive manner saliva combines the advantages of sufficient sample quantity readily available, easy test performance and good approximation of analyte content, such as blood alcohol content (BAC), for example. Alcohol detection using a saliva sample has been proven to be a sensitive and accurate method; the relationship of saliva alcohol content and blood alcohol content has been shown to be almost 1:1. Furthermore, in comparison to gas sensor-based devices for detecting alcohol in exhaled breath and typically comprising an electronic reader, detection of alcohol in a liquid sample, such as saliva, by means of a disposable test strip may sometimes offer a more convenient, simple and effective solution for a mass customer. It is therefore desirable to combine detection simplicity and cost-effectiveness of colorimetric strips with high reliability, provided by immunochemical solutions, wherein high level of reliability is attained by exerting an additional control reaction, in one disposable test strip for detection of particular analytes, preferably alcohol, in saliva.

SUMMARY OF THE INVENTION

The objective of the present invention is to alleviate at least one of the problems set forth in the background section. The objective is achieved by implementing a disposable, enzymatic assay based test strip device for colorimetric detection of an analyte compound in a body liquid sample, comprising a base support and a substrate material disposed on said base support and defining a number of reactive test zones and a reactive control zone, said test strip device further provided with a compound buffer comprising at least one chemical compound being a member of the same family as the analyte compound and/or bearing a characteristic to said family functional group, wherein each reactive test zone is configured to develop a visual indication when the concentration of the analyte compound in the body liquid sample exceeds a predetermined limit, and the reactive control zone is configured to develop a visual indication upon being supplied with the body liquid sample, wherein the substrate material defining each reactive zone is deposited with a biological ink composition comprising at least one enzyme and a chromogen; and wherein the compound buffer is disposed into the substrate material defining the reactive control zone or at least closely adjoining thereto such, that the compound buffer admixes with the biological ink composition contained in the reactive control zone when the substrate material, defining said reactive control zone or closely adjoining thereto, is supplied with the body liquid sample.

The test strip device is configured for the detection of an alcohol compound, such as ethanol, in a body liquid sample, said body liquid sample being preferably a saliva sample.

In preferred embodiment the biological ink composition is qualitatively identical for each reactive zone.

In some embodiment the compound buffer comprises an alcohol compound. In some other embodiment the compound buffer comprises a mono-, oligo- and/or polysaccharide compound selected from the group of carbohydrate compounds, comprising at least one hydroxyl group bound to carbon backbone.

In one preferred embodiment the test strip device comprises the reactive test- and control zones, each provided on an individual substrate pad fixedly attached to the base support.

In some embodiment the substrate pad, defining the reactive control zone, contains the biological ink composition and the compound buffer, provided within the substrate material in the form of stable, immiscible substances.

In some embodiments, the compound buffer is provided in the form of a film-like layer disposed in ultimate proximity to the substrate pad defining the reactive control zone, and comprises a solid alcohol compound-based polymer. In some other embodiments the compound buffer is provided in the form of a film-like layer disposed in ultimate proximity to the substrate pad defining the reactive control zone, and comprises a liquid alcohol compound, selected from the group consisting of: methanol, ethanol, glycol and glycerol, solidified by admixing thereof into a solid polymeric matrix.

In further embodiments, the test strip device further comprises at least one partition element, disposed between the reactive zones such, to prevent the biological ink composition of each reactive zone from mixing with the biological ink composition of the neighboring reactive zone(s) and/or with the compound buffer.

In still further embodiments, the test strip device further comprises a partition element in the form of a protective cover, disposed to cover exposed surfaces of the reactive zones and to separate said reactive zones from each other, which partition element comprises a number of apertures arranged over each reactive zone covered thereby.

In some other embodiment the test strip device further comprises a layer of a predetermined color, disposed between the base support and the substrate material defining the reactive zones.

In still another embodiment the test strip device is configured such, that the test- and the control reactive zones are separated from each other by means of a slot.

In another preferred embodiment the test strip device comprises the reactive test zone and the reactive control zone, deposited onto a common substrate, selected from the group consisting of: fiber-, paper- or plastic-based porous and/or mesh materials, which materials enable capillary forces driven migration of a liquid sample in a lateral direction, and wherein the reactive control zone is disposed on the common substrate subsequent to the reactive test zone in a direction of fluid flow.

In some embodiment the test strip device comprises the compound buffer deposited onto the substrate within a predetermined region subsequent to the reactive test zone and prior the reactive control zone in a direction of fluid flow. In some supplementary embodiment the test strip device may also comprise a supplementary area deposited on the common substrate within a predetermined region and spatially arranged subsequent to the reactive control zone in a direction of fluid flow; said supplementary area comprises color intensity and -shade enhancing agents, preserving agents and the like.

In some embodiments, the compound buffer and the supplementary area are configured to constitute a separate deposition layer, distinct from the one comprising the reactive zones.

In some embodiments the test strip device is configured such, that the substrate material defining each reactive zone is deposited with a biological ink composition, comprising at least enzymes alcohol oxidase and hydrogen peroxidase and a chromogenic indicator, such as 3,3',5,5'-tetramethylbenzidine.

In some other embodiments the test strip device is configured such, that the substrate material defining each reactive zone is deposited with a biological ink composition, comprising at least enzymes alcohol dehydrogenase and NAD(P)H—dependent oxidoreductase, a phosphopyridine nucleotide cofactor, such as NAD or NADP and a chromogenic indicator, selected from the group consisting of reazurin and tetrazolium salts.

In further embodiment the test strip device further comprises a flavoring agent, disposed into the substrate material.

In further embodiment the test strip device further comprises a desiccant.

In still further embodiment the test strip device further comprises at least one lamination layer.

In another aspect of the invention a method for producing substrates for the test strip device in accordance to some embodiment is provided. The method comprises stepwise incorporation of at least two different, inter-reactive substances into a common substrate material.

The utility of the present invention arises from a variety of reasons depending on each particular embodiment thereof. First of all, the invention provides a reliable and cost-effective solution for detecting at least one analyte compound from a saliva sample, which analyte compound is advantageously provided as ethyl alcohol (ethanol). The inventive solution is thus rendered to utilize saliva samples, whose collection is the most untroubled amidst body liquid samples. The solution enables semi-quantitative detection of an analyte compound present in the liquid sample in certain concentration. Furthermore, the solution offers a very high precision in determination by providing means for graded estimation of analyte concentration in a single saliva sample.

The disposable test strip of the present invention combines the simplicity of enzymatic assay based colorimetric detection of analytes with high reliability of immunochemical tests. Performing rapid analysis by means of the test strip disclosed herewith is based on an involving a liquid sample into identical, but proceeding within spatially separated zones, chemical reactions. A first reactive zone, provided herein as an actual test zone, is rendered to detect the presence of an analyte compound in certain concentration in a liquid sample and to develop a visible indication, whether an amount of an analyte present in a sample exceeds said concentration; whereas a second reactive zone is rendered to develop a visually detectable response independent on the presence or absence of an analyte in a sample. Possibility for obtaining fault responses and/or for misinterpreting the results thus obtained is reduced to zero, provided that the test had worked correctly.

From the other hand, when comparing the test strip solution disclosed herewith with existing electronic breath analyzer devices, the cost-efficiency of the present solution is evident.

The inventive method further enables production of substrates for analytical test strip devices, capable of incorporating at least two different substances, said substances, when provided as solutes, being capable to enter chemical reactions therebetween. The method thus allows producing substrates, in which mentioned substances, while being dispensed into the same substrate, preserve chemical stability and remain immiscible with each other until being caused to undergo dissolution whilst mixed with the liquid sample. The method is applicable for manufacturing reactive substrates, suitable for detection and/or analysis of a vast variety of analytes based on enzymatic and/or chemical reactions.

The term "alcohol", when utilized with regards to an analyte compound, indicates in present disclosure ethyl alcohol or ethanol, unless otherwise explicitly provided. The terms "alcohol" and "ethanol" are therefore interchangeable throughout the disclosure.

The term "enzyme" is utilized herein to indicate a biological molecule possessing certain catalytic activity in specific biochemical reaction(s) regardless of the origin and source of said molecule, i.e. whether being extracted from living cell or recombinant.

The term "element" may refer in this disclosure also to a part of a structure having no distinct physical body, such as a slot or cut-out from said structure.

The term "reactive" utilized in this disclosure with regards to a particular element is indicative of the fact, that a bio(chemical) reaction may take place within said element.

The expression "a number of" refers herein to any positive integer starting from one (1), e.g. to one, two, three etc.

The terms "first" and "second" are used herein to distinguish an element from other element and not to denote any particular order or importance if not otherwise explicitly indicated.

The terms "a", "an" and "the", as used herein, are defined to include also plural elements, unless the content clearly indicates otherwise.

Different embodiments of the present invention will become apparent by consideration of the detailed description and accompanying drawings.

BRIEF DESCRIPTION OF THE DRAWINGS

FIGS. 2A-2C illustrate the test strip device of one preferred embodiment with the compound buffer supplied into the reactive control zone by alternative methods. FIG. 2D shows various implementations for the reactive control zone, a vertical crosscut. FIG. 2E shows a more detailed arrangement of reactive substances in reactive zones within the exemplary test strip device of FIG. 2C.

FIGS. 3A and 3B show a prospective and an exploded view, respectively, of the test strip device embodied as 100, for single analyte detection. FIGS. 3C and 3D show alternative implementations for the test strip device 100.

FIGS. 8A and 8B show a prospective and an exploded view, respectively, of the test strip device of one preferred embodiment, additionally provided with an indication enhancing layer.

FIGS. 10A and 10B show test strip devices implemented in accordance with one preferred embodiment and provided with optional technical features.

DETAILED DESCRIPTION OF THE EMBODIMENTS

Figure 1A:
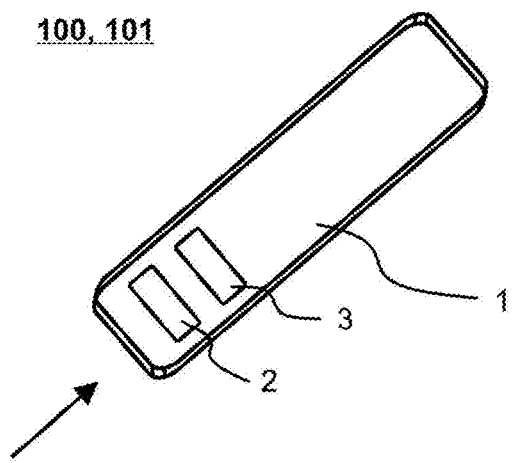
FIGS. 1A and 1B show a general representation of the test strip device 100, 101 and a detection principle thereby.

Detailed embodiments of the present invention are disclosed herein with the reference to accompanying drawings, wherein FIGS. 2-8 and 10 illustrate the preferred embodiment 100 and modifications thereof and FIG. 9 illustrates another preferred embodiment 101. The same reference characters are used throughout the drawings to refer to same members. Following citations are used for the members:

100, 100a, 100b, 101, 110, 120, 200, 210—a test strip device;
1—a base support;
2, 2a—test zone(s);
3—a control zone;
4—a compound buffer;
5, 5a, 6—partition element(s);
7—a sample application/visualization aperture;
8—a slot (mechanical cut);
9—an additional indication layer for one preferred embodiment (100);
10—a lamination layer;
11—a substrate;
12—a supplementary (control indication enhancing) area for another preferred embodiment (101);
13—a biological ink composition;
21—a flavoring agent;
22—a desiccant.

A test strip device 100, 101 (FIG. 1A) for semi-quantitative detection of analyte compounds in a body liquid sample is provided. The test strip device 100, 101 is advantageously configured to detect analyte compounds from saliva sample, said analyte compounds being preferably alcohol compounds. The test strip device is particularly suitable for detection of alcohol consumed by an individual in the form of alcoholic (ethanol containing) beverages; however, the device may be configured for detection of other, than ethanol, alcohol compounds. The test strip device 100, 101 generally comprises a base support structure 1 and a substrate material disposed on said base support and defining a number of reactive zones, indicated at FIG. 1A by reference numbers 2 and 3. A substrate material may be provided in the form of distinct, pad-like elements disposed onto the base support 1 according to a predetermined order, or it may be arranged to cover the base support entirely or a predetermined portion thereof. An arrow indicates a direction of a liquid flow, applicable only for some particular embodiment, as explained further below. The length of the exemplary test strip device advantageously ranges from 30 to 150 mm, and the width thereof ranges from 5 to 15 mm Mentioned dimensions are not, however, intended to limit the invention and may vary within the commercial implementations of the device. The test strip device 100, 101 is preferably realized as a disposable structure.

The test strip device 100, 101 is configured to visually indicate whether concentration of the analyte, such as alcohol, in saliva sample exceeds a pre-set indication limit. In the preferred embodiment the indication limit is set to a value of 0.2 permille (‰). Indication limit may be adjusted for lower or higher values, such as 0.1, 0.3, 0.5, 1.0, 1.5 or 2.0 permille, for example. Indication limits for each reactive zone are set by experimentally adjusting concentrations of the reactive components provided within said reactive zone.

The test strip device 100, 101 is configured as an enzymatic assay based colorimetric system. The system of one embodiment exploits a process of catalytic oxidation of an alcohol compound by an enzyme alcohol oxidase (AOX) (formula 1). The reaction results in release of hydrogen peroxide and an aldehyde. AOX catalyzed oxidation is further coupled with a second enzymatic reaction (formula 2), upon which hydrogen peroxide is degraded by a peroxidase enzyme in the presence of a chromogenic indicator. The system disclosed herewith advantageously utilizes horse radish peroxidase (HRP) and a single chromogenic substrate component, such as 3,3',5,5'-tetramethylbenzidine (TMB). Enzymatic degradation of hydrogen peroxide by horse radish peroxidase is accompanied by TMB oxidation. The reaction employs electron transfer from hydrogen peroxide to TMB, upon which hydrogen peroxide is reduced to water, whereas TMB is converted to an oxidized, diimine form. The oxidized TMB causes the reaction mixture to develop an intense blue color, easily detectable by eye. Operation of the test strip device 100, 101 is therefore based on the following reaction cascade:

$$C_2H_5OH + O_2 + AOX => CH_3CHO + H_2O_2 \qquad (1)$$

$$H_2O_2 + \text{substrate} + HRP => H_2O + \text{colored (oxidized) substrate} \qquad (2)$$

The system of another embodiment is based on alcohol dehydrogenase—diaphorase redox cycle. Alcohol dehydrogenase (ADH) is utilized to break down an alcohol compound (ethanol) to yield an aldehyde compound (acetaldehyde; formula 3). ADH-catalyzed reactions utilizing alcohol compounds as substrates typically require presence of phosphopyridine nucleotide cofactors, such as NAD or NADP (nicotinamide adenine dinucleotide or nicotinamide adenine dinucleotide phosphate). In an example disclosed the system is NAD-dependent.

$$C_2H_5OH + NAD^+ + ADH <=> CH_3CHO + NADH + H^+ \qquad (3)$$

The diaphorases or NAD(P)H-dependent oxidoreductases are a ubiquitous class of enzymes that catalyze the reduction of various dyes which act as hydrogen acceptors from the reduced form of phosphopyridine nucleotides, such as NADH or NADPH, for example. Diaphorase-catalyzed reaction generally proceeds in accordance with formula 4.

$$NAD(P)H + \text{substrate} => NAD(P)^+ + \text{colored (reduced) substrate} \qquad (4)$$

Diaphorase enzymes require the presence of a highly alkaline buffer (pH>8). Chromogenic substrate is therefore selected to have an optimal pH value at least 7. Suitable substrates include, but are not limited with reazurin (7-hydroxy-3H-phenoxazin-3-one 10-oxide) and tetrazolium salts, such as commercially available MTT (3-(4,5-dimethyl-2-thiazolyl)-2,5-diphenyl-2H-tetrazolium bromide), XTT (2,3-bis-(2-methoxy-4-nitro-5-sulfophenyl)-2H-tetrazolium-5-carboxanilide), TTC (2,3,5-triphenyl-2H-tetrazolium chloride), MTS (3-(4,5-dimethylthiazol-2-yl)-5-(3-carboxymethoxyphenyl)-2-(4-sulfophenyl)-2H-tetrazolium), and various WSTs (water soluble tetrazolium salts). Diaphorase enzymes are capable to reduce these substrates with the formation of chromogenic products formazans.

At least two reactive zones can be identified within the substrate material disposed onto the base support 1 of the test strip device 100, 101 (FIG. 1A). In one preferred embodiment each reactive zone is implemented to confine spatially and functionally to a corresponding pad-like fragment of the substrate material. In another preferred embodiment each reactive zone is implemented to confine spatially and functionally to a predetermined area within a larger portion of the substrate material. Independent on implementation each reactive zone is deposited with a set of bio (chemical) reactants, further referred to as a "biological ink". Qualitative composition of said biological ink in each reactive zone is identical. For clarity purposes a first reactive zone is further defined as a test zone 2 and a second reactive zone—as a control zone 3, respectively. The test zone 2 and the control zone 3 advantageously constitute a reactive area, which also serves as a sample application area.

Reactive zones 2 and 3 share an identical set of bio (chemical) reactants, comprising, in one embodiment, at least enzymes alcohol oxidase and horse radish peroxidase, and a chromogen TMB. In another embodiment the reactive zones 2 and 3 may comprise, in addition to enzymes alcohol dehydrogenase and diaphorase, also nicotinamide adenine dinucleotide (NAD+), acetaldehyde binding agents (hydroxylamine or di-amine compound, such as 1,2-diaminoethane, for example), an alkaline buffer (pH>8) and a suitable chromogenic substrate. Optional components for both AOX- and ADH-based embodiments may include stability enhancing agents, such as mannitol, dextrane(s), sodium azide and/or surfactants, such as Triton X, for example.

The test zone 2 hosts a test reaction, allowing for an actual detection of the analyte of interest in a body liquid sample and resulting in development of a visual indication within said test zone 2 in case concentration of the analyte compound in the body liquid sample exceeds a predetermined limit. The control zone 3, in turn, hosts a control reaction, which results in development of a visual indication within said control zone 3 independent on the presence or absence of the analyte in a body liquid sample.

The control zone reaction is anticipated by provision of a compound buffer 4, comprising a chemical compound which advantageously belongs to the same family as a detectable analyte compound and/or bears a functional group characteristic of that family of compounds. The compound buffer may consist of or comprise reagent(s) same or equivalent to the analyte compound. In the preferred embodiments the compound buffer 4 comprises an alcohol compound, or a compound bearing a characteristic to alcohol compounds' family hydroxyl functional group to ensure that the control reaction proceeds via the same mechanism as a test reaction.

Figure 1B:
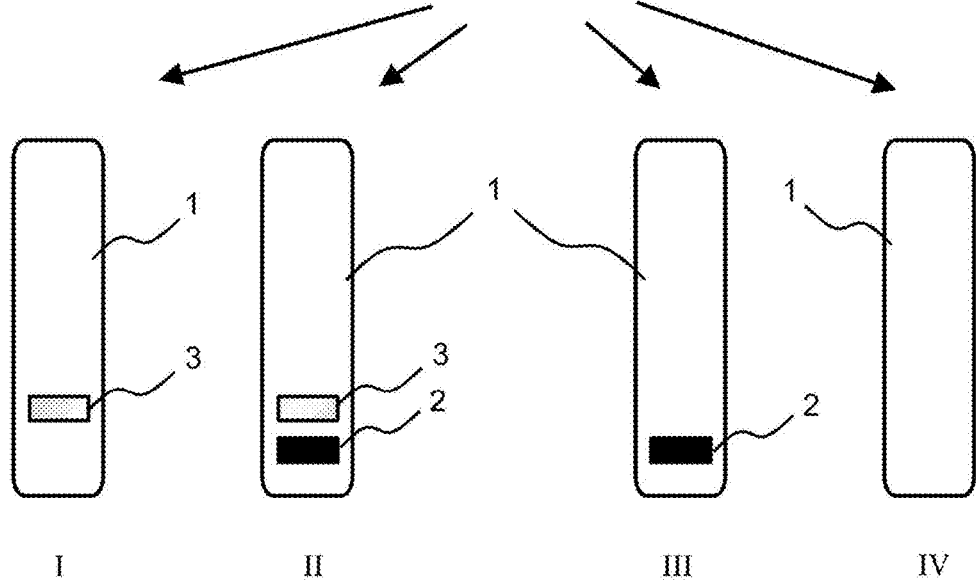

Such an arrangement enables development of total four scenarios, depending on whether a predetermined amount of an analyte compound is present in a body liquid sample, such as saliva (FIG. 1B). Scenarios indicated by Roman numerals I and II indicate, respectively, "negative" and "positive" results obtained by properly functioning tests. Visual indication within the test zone 2 may be observed when the concentration of the analyte compound in the body liquid sample exceeds a pre-set indication limit. This indication must be accompanied with a visual indication within the control zone 3 (Scenario II) to ensure a correct performance of the test strip device. Whether visual indication is observed only within the control zone 3 (Scenario I), this is indicative of the fact that either no detectable analyte is present in the sample, or concentration thereof falls below the pre-set indication limit. Scenarios indicated by Roman numerals III and IV illustrate the examples of an erroneous system: visual indication is observed only within the test zone 2 (Scenario III) and the test strip is blank (Scenario IV). In any case, saliva sample is advantageously applied onto the test strip 100, 101 such, to target the reactive zones 2 and 3. Scenarios I-IV are briefly summarized in the Table 1 below.

During test strip device manufacturing process the substrate material is deposited with the biological ink composition, designed to comprise at least enzymes and chromogen(s). In ADH—diaphorase system the presence of a phosphopyridine nucleotide cofactor is also required. Bio(chemical) components are preferably pre-dissolved in suitable buffer solution, such as phosphate-buffered saline (PBS), for example. Said biological ink composition may include also various supplementary agents, such as color shade—and intensity enhancing substances, preserving agents and the like. Dependent on the embodiment deposition can be realized via printing, dispensing and/or coating.

TABLE 1

Test results for alcohol detection from a saliva sample obtainable with the test strip device 100, 101.

| Scenario I | Scenario II |
| --- | --- |
| "Negative": Visual indication observed only in the control zone 3 Alcohol content in blood is zero or falls below a pre-set indication limit, e.g. below 0.2 permille; test result is negative, the test strip device functions properly. The test zone 2 remains colorless, whereas the control zone 3 develops blue or other color upon mixing of the sample with an alcohol-containing buffer thus triggering an embodiment-dependent enzymatic cascade. Colorimetric reaction takes place largely within the control zone 3. | "Positive": Visual indication observed in the test zone 2 and in the control zone 3. Alcohol content in blood exceeds a pre-set indication limit, e.g. 0.2 permille; test result is positive, the test strip device functions properly. Both test zone 2 and control zone 3 develop blue or other color as a result of embodiment-dependent enzymatic cascades, proceeding within the test zone 2 and the control zone 3. |
| Scenario III | Scenario IV |
| Visual indication observed only in the test zone 2. | No visual indication, both reactive zones remain colorless. |

Test result is erroneous; the test strip device does not function properly.

The preferred embodiments of the test strip device will further be described in more detail with reference to FIGS. 2-10.

One preferred embodiment 100 of the test strip device is shown on FIGS. 3A and 3B, while the fragment of said device with the reactive zones 2, 3 is shown in more details on FIGS. 2A-2C. The test strip device 100 comprises a rigid or semi-rigid base support structure 1, provided with two reactive zones 2 and 3, corresponding to test- and control zones, as described above. Each reactive zone is implemented in the form of distinct pad-like element, defined as a fragment of the substrate material disposed onto the base support 1. For clarity purposes numerical indication of the substrate material per se is herein omitted. The base support 1 is preferably implemented from plastic polymer; however other materials, such as carton board, various (bio)polymeric and plastic composites and the like are not excluded, as long as the element 1 maintains its supporting function. Each pad-like element thus consists of the substrate material, capable to incorporate and/or to preserve required (bio)chemical reagents, and is further referred to as a "substrate pad".

Substrate material is selected from the range of materials, capable to efficiently absorb a sufficient amount of liquid, such as saliva, for chemical reaction(s) to initiate and to proceed. Substrate porosity is therefore an important factor to consider. For example, some porous substrates may turn translucent upon application of liquid samples thereto. Whatman® Fusion membranes may be mentioned as one of the exemplary substrate materials.

Printing may be achieved by conventional methods, such as gravure printing, flexography printing, screen printing, offset printing, inkjet printing and the like.

During test strip device manufacturing sheets of substrate material, pre-deposited with the biological ink composition, are cut into pieces or pads of suitable size and further attached to the base support. Alternatively, pre-cut substrate pads may be attached to the base support prior to biological ink deposition process. Attachment of the substrate to the base support is preferably realized by means of adhesive or glue; however, any other appropriate means are not excluded. Regardless of a manufacturing method general chemistry and therefore qualitative composition of aforesaid biological ink remains the same, although it may comprise slightly different amounts of each reagent.

In embodiment 100, shown on FIGS. 3A and 3B, the first reactive zone, defined as the test zone 2, and the second reactive zone, defined as the control zone 3, spatially and functionally confine to corresponding individual substrate pads, deposited with the biological ink as disclosed above and fixedly attached to the base support 1. Qualitative composition of said biological ink, utilized for application onto each mentioned substrate pad, is preserved the same.

The control zone, represented in this embodiment by a "control" substrate pad 3, further comprises the compound buffer 4. In one embodiment the compound buffer 4 is provided as a separate layer structure disposed to adjoin the substrate pad 3. FIG. 2A thus shows a compound buffer provided as a separate, tape-like film or layer 4, positioned underneath the substrate pad 3. The compound buffer 4 is herein provided as a distinct layer element, separable from an actual substrate pad structure. Disposition of the buffer layer 4 underneath the substrate pad 3, as shown on FIG. 2A and also on FIGS. 3A and 3B, is still exemplary, since the tape-like buffer layer 4 may be positioned on the top of the substrate 3 (see FIGS. 3C and 3D) or next to it. The only critical requirement for the disposition of the layer 4 with regards to the substrate pad 3 is its ultimate proximity thereto. The buffer layer 4 must be positioned sufficiently close to the substrate pad 3, such, that alcohol or the other hydroxyl group containing compound contained in the compound buffer 4, can mix with the biological ink composition, provided within the substrate pad 3 upon wetting said substrate pad to initiate enzymatic reaction(s).

In one other embodiment the compound buffer 4 is inseparably integrated into the substrate pad 3. FIGS. 2B and 2C show alternative embodiments for the test strip device 100, differing by disposition and/or application of the compound buffer 4 within the control zone. The test strip devices embodied as 100a and 100b comprise the control zone 3 having the compound buffer 4 dosed directly therewithin and inseparable therefrom.

FIG. 2B shows an embodiment 100a, whose technical realization is such that the compound buffer 4 is applied directly to the "control" substrate pad 3 having sufficient porosity to receive and evenly distribute said buffer therealong. The buffer 4 thus forms a layer-like internal structure within the substrate material forming the pad 3. FIG. 2C shows an embodiment 100b, wherein the compound buffer 4 is applied directly to the substrate pad 3 such, that said buffer 4 resides within a spatially restricted area inside the pad 3. The embodiments 100a and 100b enable application of the biological ink composition onto the buffer-deposited substrate or, alternatively, application of the buffer 4 onto the substrate, pre-deposited with the biological ink composition. Structures 100a, 100b enable integration of the compound buffer 4 and the biological ink composition within the same substrate without mixing of these two substances therebetween.

FIG. 2D shows various implementations for the substrate pad 3 in more detail. In particular, FIG. 2D shows disposition of the biological ink composition, indicated by a reference number 13, with regards to the compound buffer 4 within said substrate pad 3. For test strips devices embodied as 100a, 100b, it is important to understand, that while at least two different, inter-reactive substances 4, 13 are deposited into the same substrate material (herein, substrate pad 3), said substances remain chemically stable and, therefore, immiscible with each other until being contacted with the liquid sample. The substrate pad 3, as provided for some embodiments, thus forms an inseparable structure, incorporating at least two different substances, normally possessing chemical reactivity towards each other, but being preserved in chemically inert (stable) state until at least one of said substances is activated by dissolution in the body liquid sample. In this regard, at least one of said substances is provided water soluble. By terms "chemically inert" and "stable" we refer herein to incapability of said two substances 4, 13 to mix and/or react with each other until at least one of them is dissolved in the liquid sample. Any of the test strip devices embodied as 100a, 100b are therefore configured such that the substrate pad defining the reactive control zone 3 contains the biological ink composition 13 and the compound buffer 4, provided within the substrate material in the form of stable, immiscible substances, until being contacted with the body liquid sample.

High spatial precision for aforesaid disposition of the buffer 4 in embodiments 100a, 100b may be attained by optimized printing techniques. In these embodiments the substrate pad 3 is designed such, that a predetermined space is reserved for the application of the biological ink composition 13 thereto. The biological ink composition 13 contains all the reagents required for the enzymatic reaction to take place. Dependent on a manufacturing process the biological ink composition 13 may be applied either prior to (e.g. FIG. 2D, iii-iv) or after applying the compound buffer 4 onto the substrate pad 3 (e.g. FIG. 2D, ii). Alternatively, deposition of the biological ink composition 13 and the compound buffer 4 may be implemented as parallel processes; in that case the compound buffer 4 will be printed alongside the biological ink composition 13 (FIG. 2C; FIG. 2D, i). Printing pattern of the compound buffer 4 may vary; it may encircle printed biological ink composition 13, for example (not shown). Optimization of printed patterns is done with regards to technical aspects of a printing process, including mixing ratio of the sample with regards to the compound buffer and the biological ink composition.

FIG. 2E thus illustrates the test strip device implemented according to the exemplary embodiment 100b and comprising the "test" substrate pad 2 deposited solely with the biological ink composition 13 and the "control" substrate pad 3 deposited with the biological ink composition 13 and the compound buffer 4. The control pad 3, as shown on FIG. 2E, is constructed in accordance with the example (i) shown on FIG. 2D. Still, in practice any of the examples (i-iv) shown on FIG. 2D may be utilized for constructing the test strip device 100a, 100b in a manner shown on FIG. 2E.

The compound buffer 4 is preferably selected from the chemical compounds belonging to the same family as an analyte compound, which can be recognized by the presence of a characteristic functional group that strongly determines the physical and chemical properties of the compounds that belong to said family. In one embodiment the compound buffer 4 therefore comprises an alcohol compound. An alcohol compound may be generally represented by any organic compound with the general formula ROH, wherein R represents an alkyl group made up of carbon and hydrogen in various proportions and OH represents one or more hydroxyl groups. Suitable alcohol compound may include one, two, three or more hydroxyl groups. Exemplary monohydric alcohol compound (including one hydroxyl group) may be represented by methanol, ethanol, isopropanol and various propyl, butyl and amyl alcohols; exemplary dihydric alcohol compound (with two hydroxyl groups)—by glycols; and exemplary trihydric alcohol compound (with three hydroxyl groups)—by glycerol.

For example, in order to implement the compound buffer 4 in the form of a separate layer structure (FIGS. 2A, 3A, 3B) the alcohol compound is preferably selected from the group of non-volatile alcohol compounds. The buffer 4 may thus be provided in a solid (polymeric) form, such as polyethylene glycol (PEG) or polyvinyl alcohol (PVA), for example. Alternatively a liquid state, short-chain alcohol-containing compound, selected from the group consisting of: methanol, ethanol, glycol, glycerol and the like, may be admixed to a long-chain polymeric matrix, such as PEG or acrylate, thus imparting necessary solidness to an otherwise liquid substance. Short-chain alcohols ensure high response levels of the control reaction; molecular mass of the alcohol-containing compound also has an effect onto the control reaction response.

In another embodiment the buffer 4 comprises a carbohydrate compound in the form of a mono-, oligo- and/or polysaccharide compound, comprising at least one hydroxyl group bound to a carbon backbone. Said carbohydrate compound is preferably selected from the group consisting of: glucose, fructose, galactose, sucrose, lactose, maltose, trehalose (mycose), and/or mixtures and polymeric forms thereof. The same functional group(s) (hydroxyl) will undergo the same or similar chemical reaction(s) regardless of the class of the compound containing thereof.

Other possible components potentially suitable for obtaining the compound buffer 4 for any embodiment disclosed hereby include, in some embodiments, polyvinylpyrrolidone (PVP), which, however, does not include an alcohol group, but a ketone group; and/or any other appropriate hydroxyl group(s) containing compound, which is either non-volatile by nature or possesses an imparted non-volatility by being admixed into a suitable matrix, for example.

Consistency of the compound buffer 4 is therefore an important factor to consider when selecting a method to supply the control zone 3 with the said compound buffer. Generally, the compound buffer 4 may be applied onto the control zone by any appropriate deposition method, such as dispensing, coating and/or printing.

A method for manufacturing substrates for the test strip devices embodied as 100a, 100b is further provided. Said method enables production of substrate pads, which incorporate at least two different, inter-reactive substances into a common substrate material such that said substances are preserved in the substrate material in stable, immiscible form until being contacted with the body liquid sample.

For production of substrates for the test strip devices embodied as 100a, 100b, at least one of the substances, selected from the group consisting of: the biological ink composition 13 and the compound buffer 4, is soluble in water or at least miscible with water. In some embodiments both the biological ink composition 13 and the compound buffer 4 are water soluble. In order to incorporate said water soluble substances into a substrate material, viscosity thereof is increased by utilizing any appropriate viscosity increasing-/thickening agent. The viscosity increasing agent is preferably selected such, to additionally impart high degree of homogeneity/consistency to the resulting blend. Application of the reactive substances 4, 13 onto the substrate material (herein, substrate pad 3) is achieved as sequential or parallel processes.

In similar manner, the production of the "test" substrate 2 (i.e. the substrate, comprising solely the biological ink composition 13) and the "control" substrate 3 (i.e. the substrate, comprising both the biological ink composition 13 and the compound buffer 4) may be implemented as sequential or parallel processes. The substances 4, 13 are applicable by at least one method selected from the group consisting of: screen printing, dispensing or roll-to-roll printing, such as flexography, gravure printing methods and anilox printing. Utilization of any other appropriate method is still not excluded. Upon stepwise supplying the substrate material by the reactive substances 4 and/or 13, each of said substances is preferably dried before proceeding to the next stage. Preferred drying time is 5-60 minutes, preferably 10-20 minutes, and preferred drying temperature is 35-65 degrees Celsius, preferably 40-60 degrees Celsius.

It should be clear to those skilled in the art that the processes for the selection of substrate pad materials, application of the biological ink composition thereto and supply the control zone with the compound buffer, as well as disposition of said substrate pads onto the base support, are largely design- and/or functionality dependent. Alternative layout for the reactive test- and control zones, provided in the form of substrate pads, for the exemplary test strip device 100 is shown on FIG. 3D. The "control" substrate pad 3 may thus be disposed at the end portion of the base support 1. To ensure correct operation of the test strip devices 100, 100a, 100b essentially equal amounts of the liquid sample should be applied onto each of the reactive zones 2 and 3. Whether this is the case enzymatic reactions proceed within each reactive zone independently and the liquid sample dosed into each reactive zone remains within the borders defined by the appropriate substrate pad.

In order for aforesaid enzymatic reactions to proceed independently, the reactive zones 2 and 3 must be spatially separated from each other. In one embodiment separation is implemented by means of a partition element. FIGS. 3A and 3B show a test strip device, embodied as 100 and provided with a partition element 5 mounted onto the base support 1 into a space between the substrate pads 2 and 3 to such an extent, to prevent admixing of the compound buffer 4 provided within the control zone 3 with the reagents, contained in the test zone 2. Illustrated by FIGS. 3A and 3B embodiment 100 is advantageously configured to utilize a partition element 5 produced from a tape-like material and mountable into a space between the substrate pads 2 and 3. Such a tape-like material is provided with an adhesive surface, capable of adhering to the base support 1, thus creating a solid barrier for preventing the reagents of the neighboring reactive zones to unintentionally mix into each other.

Alternatively, the partition element 5 may be realized as a piece of a Teflon fabric, insertable in between the individual substrate pads 2 and 3 (now shown). Another alternative arrangement may be realized by utilizing a curable adhesive, such as a UV-curable adhesive, applicable directly onto the substrate pad(s) at the particular locations to create one or more partition walls within said pad(s). Due to a porous nature of the printable substrate, said curable adhesive easily penetrates therethrough and hardens upon being exposed to curing radiation, for example. Such an arrangement enables creating several reactive zones on a single substrate pad without cutting said pad. A single substrate pad may thus incorporate both test- and control zones, separated one from another by curable adhesive.

Figure 4A:
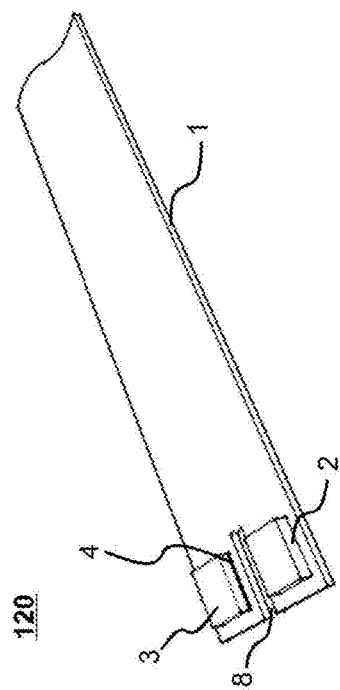
FIGS. 4A and 4B show a prospective and an exploded view, respectively, of the test strip device, embodied as 110, for single analyte detection.
Figure 4B:
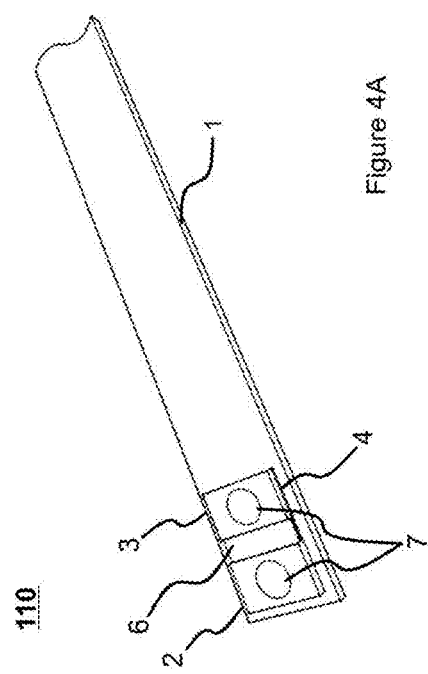

FIGS. 4A and 4B show the test strip device, embodied as 110 and provided with the partition element 6 in the form of a protective cover. The partition element 6 may be implemented in the form of a tape-like element, adapted to tightly cover both substrate pads 2 and 3 and the region therebetween. The tape-like material may be the same material, as disclosed for the tape-like partition element 5 (FIGS. 3A, 3B). An adhesive surface of the partition element 6 closely adjoins the exposed surfaces of the substrate pads 2 and 3, descending also into a gap region provided between said pads. In this gap region the partition element 6 tightly adjoins the surface of the base support 1, onto which the substrate pads 2 and 3 are originally arranged, thus prohibiting the reagents provided within said substrate pads 2 and 3 from mixing with each other. The partition element 6 in the form of a protective cover may also by manufactured as a solid- or semi-solid piece from other appropriate materials and shaped accordingly.

In order to enable sample application onto the substrate pads 2 and 3, defining test- and control zones, respectively, the partition element 6 comprises apertures 7 arranged over each substrate pad. Apertures 7 therefore serve for both sample application onto the test strip device 110 and for enabling visualization of test results; apertures 7 may thus be referred to as indication windows. FIGS. 4A and 4B show apertures 7 of circular shape, which however, should not be considered as a limiting factor, since the shape of said apertures 7 may easily be modified to rectangular, triangular, elliptic and/or any other arbitrary shape, depending on design purposes.

A non-adhesive (user-directed) surface of the tape-like material, constituting the partition element 6, may further bear a variety of user-assistance and/or guidance marks, such as literal or graphical indicators of the test- and the control zones, for facilitating the procedures of sample application and reading of test results. Such marks may be pre-printed on the tape before applying it onto the test strip device or applied to the ready-made test strip device prior to packaging.

Along with prohibiting the reagents from mixing, the tape-like material, constituting the partition elements 5 and 6, performs another important function of guiding a liquid sample towards the reactive zones 2 and 3. The tape-like material, generally arranged between the substrate pads 2 and 3, facilitates flow of a liquid sample in the directions of the actual reactive zones 2 and 3. This principle may be equally applied for both the partition element 5, arranged to merely separate the reactive zones, and for the partition element 6, provided in the form of a film, tightly covering the reactive substrate pads 2 and 3 and the gap region therebetween. Aforesaid function is particularly useful, when the liquid sample is applied approximately onto the middle of the reactive/sample application area, as defined elsewhere.

It should be made clear, that any of aforesaid partition elements 5, 6 may be utilized also with regards to any of the embodiments 100*a*, 100*b* (FIGS. 2B, 2C).

Figure 5A:
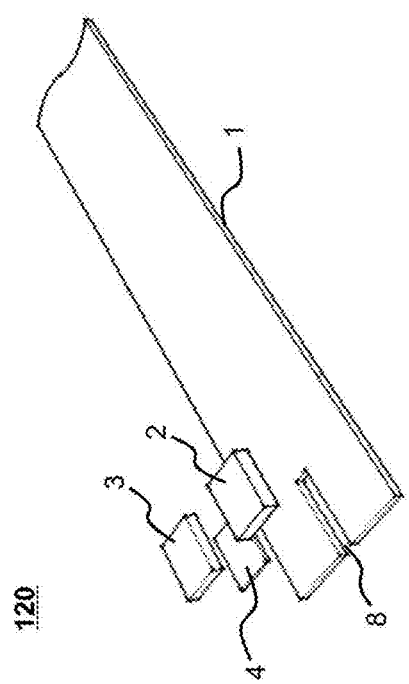
FIGS. 5A and 5B show a prospective and an exploded view, respectively, of the test strip device, embodied as 120, for single analyte detection.
Figure 5B:
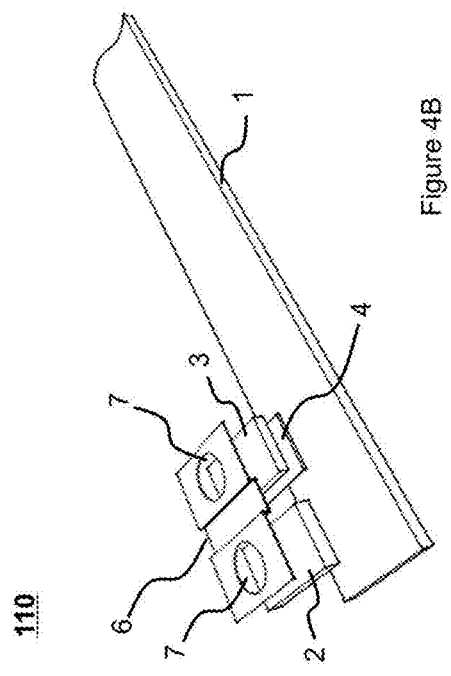

FIGS. 5A and 5B show the test strip device, embodied as 120. Separation of the test- and the control zones from each other is implemented herein by means of cutting the base support 1 at one end thereof to create a slot 8. Slot 8 performs the same function as partition elements 5 and 6 in the embodiments 100 and 110, namely creates a physical barrier between the reactive zones 2 and 3. Corresponding substrate pads 2 and 3 are therefore advantageously positioned on either side of the slot 8. Test strip devices embodied as 100*a* and 100*b* may be modified in similar manner. Manufacturing of the test strip device of FIGS. 5A and 5B is therefore advantageous in terms of cost-effectiveness, since additional material costs may thus be omitted. FIGS. 5A and 5B show an optimal profile and location for the slot 8 with regards to the test strip device 120; however, for those skilled in the art it should be clear, that any other alternative is possible as far as the slot 8 fulfills its main function, i.e. prevents the reagents of the test- and the control zones from mixing.

The embodiment 120 as shown on FIGS. 5A and 5B may still comprise the tape-like material (not shown), applied onto the exposed reactive zones 2 and 3 for protective purposes, for further preventing the reagents from mixing, for directing the liquid sample towards said reactive zones and/or for providing additional guidance to the user.

Separation of the test- and the control zones from each other and therefore prevention the reagents contained therewithin from mixing may further be implemented by means of any other mechanical and/or heat treatment.

Utilization of the partition element(s) may be completely omitted also by disposing the test- and the control zones sufficiently far away from each other, e.g. on the opposite ends of the base support 1. FIGS. 3C and 3D show exemplary test strip devices embodied as 100 with the partition element excluded from the implementation.

Figure 6A:
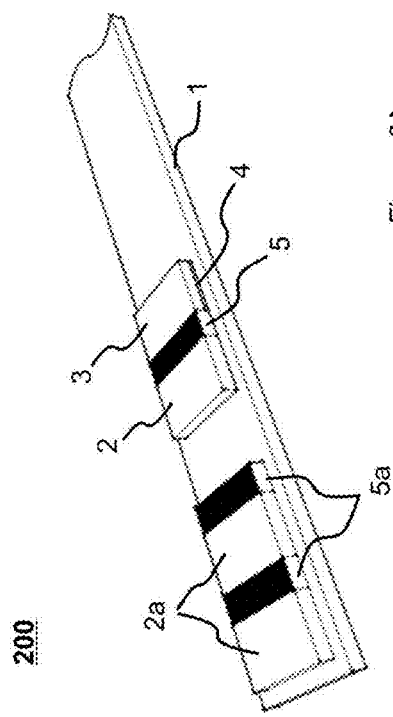
FIGS. 6A, 7A and 6B, 7B show a prospective and an exploded view, respectively, of the test strip devices, embodied as 200 and 210 for multiple detections.
Figure 6B:
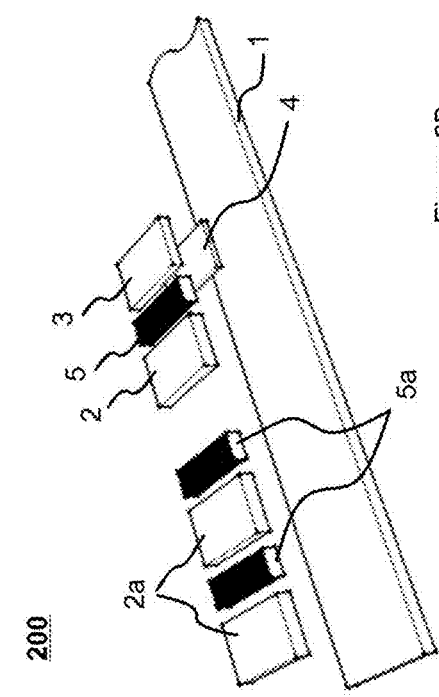

FIGS. 6 and 7 illustrate the test strip device for so called multiple detections. By "multiple detections" we refer to the detection of a single analyte compound in multiple concentrations. FIGS. 6A and 6B thus show the test strip device, embodied herein as 200 and generally representing one of the embodiments 100, 100*a* or 100*b*, modified for performing multiple detections and therefore comprising a number of test zones exceeding one. The device 200 is designed to enable high-precision determination of analyte concentration in liquid saliva sample. The device 200 comprises the base support 1, the control zone 3, configured as a corresponding substrate pad provided with the compound buffer 4, and at least two test zones 2, 2*a*, each pre-set with its own, specific indication limit FIGS. 6A and 6B show the device 200 comprising three test zones, each of these is provided as an individual substrate pad deposited with the biological ink composition. At a first glance all the substrate pads 2, 2*a* are identical. The difference lies in quantitative composition of the biological ink, utilized for printing, and provided as an amount of enzymes, chromogenic indicators and other (bio) chemical reagents contained in said ink and the ratios therebetween. Qualitative or chemical composition and, consequently, the reactive chemistry remains the same in all substrate pads, including the substrate pad 3, constituting the control zone. Adjusting the quantities of (bio)chemical components contained in the biological ink composition enables pre-setting indication limits specific for each test zone. In one exemplary embodiment, the test strip device 200 may be configured such, that the test zone 2 is pre-set to detect an analyte, such as alcohol, whose concentration is equal or exceeds 0.1 permille, whereas each of the remaining test zones 2*a* is pre-set to detect the same analyte in concentrations 0.2 and 0.5 permille, correspondingly.

Manufacturing of the test strip device 200 involves above-mentioned processes of biological ink deposition onto a membrane, by means of e.g. printing, dispensing and/or coating, as disclosed above. Printing processes utilize biological inks, whose composition is quantitatively adjusted to provide required detection/ indication limits. In the test strip device 200 the test substrate pads 2, 2*a* are advantageously grouped by ascending or descending indication limit order with regards to the "control" substrate pad 3. The arrangement of the substrate pads 2, 2*a* and 3 on the base support 1 may still be arbitrary.

The test strip device 200 further comprises partition elements 5, 5*a*. Said partition elements may be realized in the same manner as partition element 5 disclosed for the embodiment 100 (FIGS. 3A, 3B).

Figure 7A:
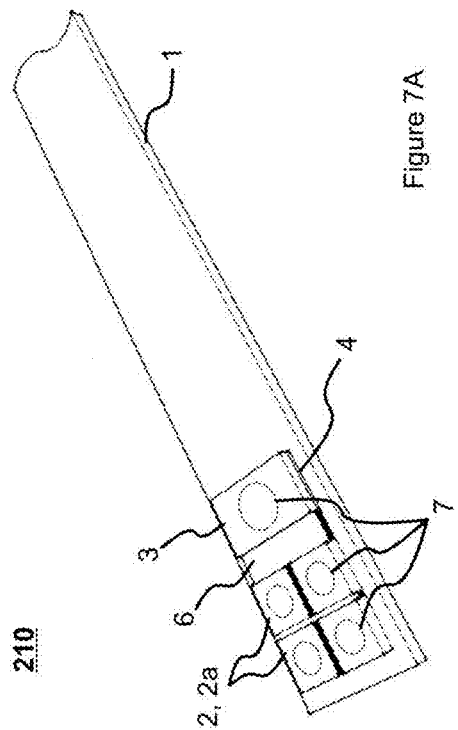
Figure 7B:
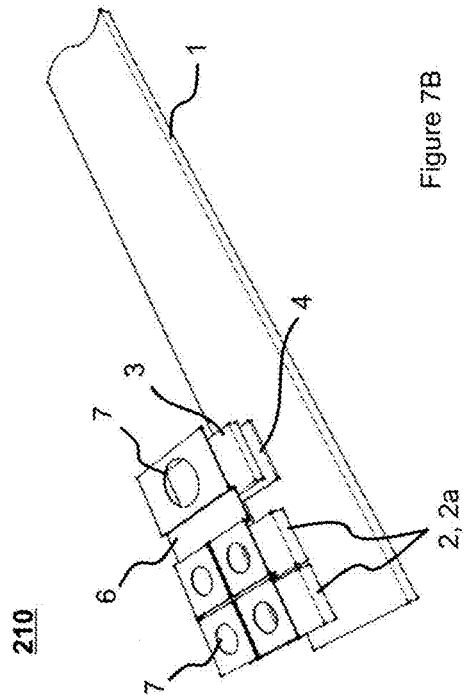

An alternative embodiment 210 for multiple detections is shown on FIGS. 7A and 7B. The test strip device 210 is implemented on the basis of the device 110 (FIGS. 4A, 4B), modified for multiple detections. In the device 210 the reactive zones 2, 2*a* and 3 are physically separated from each other by a continuous partition element 6, provided in the form of a protective cover and manufactured in the same manner as for embodiment 110. Said partition element 6 is advantageously provided with a number of apertures 7, as already disclosed for the embodiment 110.

It should be noted, that amounts and ratios of (bio) chemical components selected for deposition onto the control zone(s) forming substrates are experimentally adjustable for each specific indication limit, set up for the corresponding "test" substrate(s)/substrate pad(s). For example, the quantitative composition of the control zone may vary in two different test strip devices each having indication limit pre-set to e.g. 0.2 and 0.5 permille, correspondingly. Therefore, in all embodiments disclosed thus far, the test substrate pad 2 may contain slightly different amounts of enzymatic, chromogenic and/or other bio(chemical) components in comparison with the control pad 3, while the qualitative (chemical) composition thereof remains the same.

FIGS. 8A and 8B illustrate the test strip device 100, additionally comprising means for indication that sufficient amount of a sample, such as saliva sample, has been applied onto the test- and/or the control zones. Said means may be implemented in the form of an additional layer 9 sandwiched between the base support 1 and the substrate pads 2 and/or 3. Whether the substrate pad 3 is provided with a film-like compound buffer 4, as shown on FIGS. 8A, 8B, the layer 9 is disposed underneath said film-like buffer. The layer 9 is supplied with a pre-determined color, clearly distinct from the color shades of other elements provided within the test strip device. Such coloration of the layer 9 is essential for indication functions performed thereby. The layer 9 may be provided in the form a tape-like structure, for example; alternatively, said layer may be deposited (e.g. printed) directly onto the base support 1.

The test strip device, comprising the layer 9, exploits physical properties of the porous substrate, as well as optical properties of the sample. Whether the test strip device is further provided with the layer 9, the substrate material utilized for manufacturing pads 2 and 3, is advantageously selected such, to acquire a property of transparency or semi-transparency/translucency when sufficient amount of liquid sample is applied thereto. By turning transparent or semi-transparent/translucent said substrate materials renders visible a colored surface located underneath.

The test strip device 100 comprising the layer 9 operates as follows. 1) Whether an amount of the sample applied onto the reactive area is not sufficient, the substrate pads 2 and 3 will preserve their original shades; colorimetric indications within the test- and/or control zones are possible. 2) Whether an amount of the sample applied onto the reactive area is sufficient, but the sample does not contain sufficient for detection amount of analyte, the substrate pads 2 and 3 will turn translucent and expose the colored layer 9, located underneath; colorimetric indication within the control zone will be developed. 3) Whether an amount of the sample applied onto the reactive area is sufficient and whether the sample contains sufficient for detection amount of analyte, the substrate pads 2 and 3 will turn translucent, expose the colored layer 9 located underneath and further develop a colorimetric indications within both reactive zones. For obtaining as clear visible indication as possible the color of the layer 9, its shade and intensity, should be experimentally adjusted for each enzymatic system utilized herewith.

For those skilled in the art it should be clear that any of the embodiments disclosed thus far may comprise the layer 9. The layer 9 may be deposited under the test- and/or the control zones.

FIGS. 10A and 10B further show test strip devices implemented in accordance with any sample pad technique based embodiment disclosed thus far and provided with optional technical features. FIG. 10A thus shows an exemplary test strip device, embodied as 100, 110, further comprising a flavoring agent 21, provided on a separate substrate of its own. Said flavoring agent may be represented by any suitable compound or a combination of compounds, capable of imparting a recognizable flavor and/or taste to the substrate material containing thereof. Some exemplary recognizable flavors may include that of citrus, berries, mint, cocoa, caramel, liquorice and the like. The flavoring agent 21, provided on a separate substrate, is made available to the user via at least one aperture positioned over said substrate. FIG. 10A shows three small apertures in a tape-like protective cover 6, positioned over the substrate with the flavoring agent 21 dosed therein. Substrate material for the flavoring agent 21 and methods of application thereof may differ from the ones, applicable for the reactive substances, provided as the biological ink composition 13 and the compound buffer 4.

Alternatively, the flavoring agent may be provided on any or all of the substrate pads defining test- and/or control zones 2, 2a, 3 (not shown). By careful selection of a flavoring agent for dosing onto the reactive zone(s), an improved functionality of the test strip device may be achieved. Thus, contained in a number of flavoring agents ascorbic acid, when mixed into water soluble biological ink composition, comprising enzymes alcohol oxidase and horse radish peroxidase, restricts amount of hydrogen peroxide generated during the chemical reaction of said enzymes with the alcohol-containing analyte. By utilizing ascorbic acid based flavoring agents indication range may thus be adjusted with high precision.

FIG. 10B shows an exemplary test strip device 100 additionally comprising a desiccant 22. One of the preferred desiccants/drying agents is silica gel; however, utilization of any other appropriate substance is not excluded. Provision of the test strip device comprising the desiccant 22 may confine to implementations (i-iii, FIG. 10B), wherein the desiccant 22 is: (i) integrated into an adhesive used for attaching the substrate pads 2, 3 to the base support 1; (ii) provided in the form of separate solid structure(s) disposed in instant proximity to the substrate pads 2, 3 and/or therebetween; and (iii) provided in the form of a separate solid structure disposed remotely from the substrate pads 2, 3. Alternatively, the desiccant may be deposited directly to the material used for manufacturing the base support 1 (not shown).

Any of the test strip devices 100, 100a, 100b, 110, 200, 210 disclosed thus far may further be surface-laminated to attain a sleek, customer attractive appearance. An exemplary laminated device is shown on FIG. 10A. For embodiments 110, 210, surface lamination may be realized in the form of a protective cover 6 or in the form of an additional lamination layer 10. Lamination additionally allows for or at least facilitates application of various utility and/or decoration markings, logos and other information onto the test strip devices.

All embodiments disclosed thus far are based on a substrate pad technique, wherein the liquid sample, once applied onto a reactive zone, defined by an individual substrate pad, uniformly distributes within said substrate pad due to the porous nature thereof. The liquid sample, therefore, remains within the pad, excluding the fact that at the stage of application thereof liquid travels vertically downwards within the pad and simultaneously spreads sideward to an extent set up by the boundaries of the substrate pad.

Figure 9A:
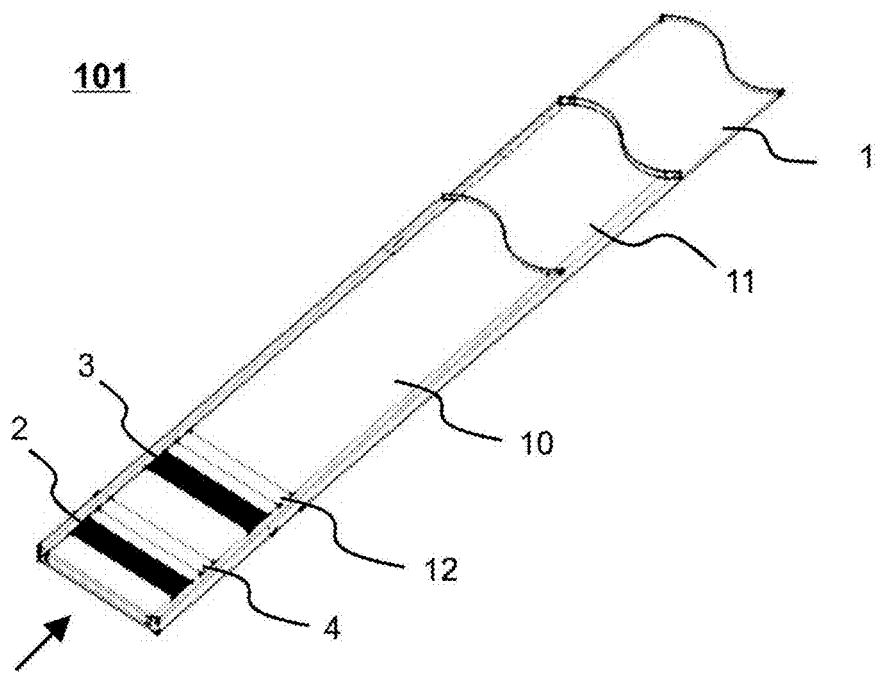
FIGS. 9A and 9B shows a prospective and an exploded view of the test strip device, embodied as 101, for single analyte detection employing lateral flow technique.
Figure 9B:
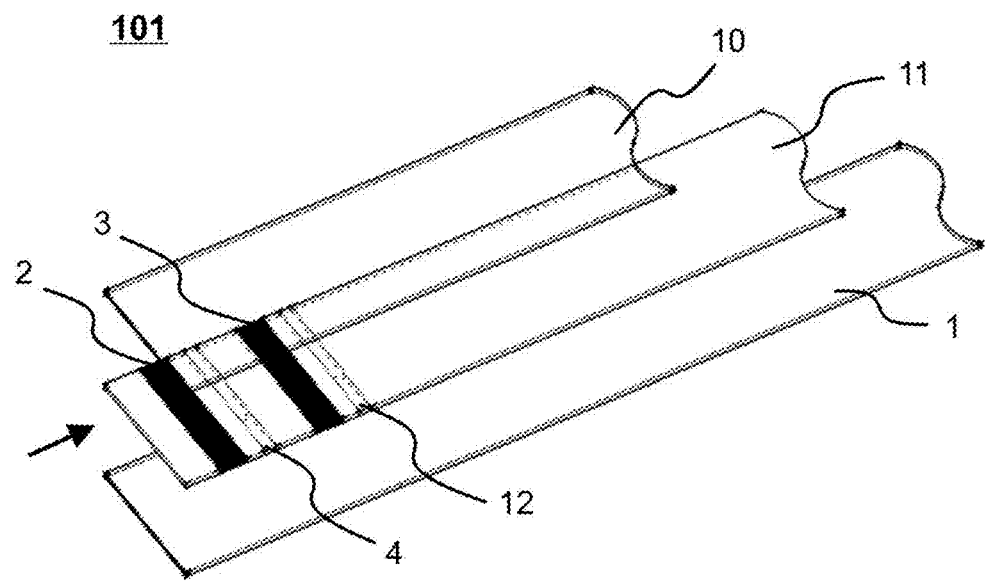

FIGS. 9A and 9B illustrate another preferred embodiment 101 of the test strip device. The device 101 exploits the principles of lateral flow, wherein fluid applied thereto migrates in longitudinal (lateral) direction driven by capillary forces. Whereas in the device embodied as 100 and modifications thereof the disposition of the test—and the control zones with regards to each other is arbitrary, the test strip device 101 requires that the arrangement of the test—and the control zones on a plane is complied with a pre-determined order. Provision of the test strip device 101 is such that the liquid sample applied thereto always flows first via the test zone 2, further migrating towards the control zone 3 in a direction of a fluid flow indicated on FIGS. 9A, 9B by arrow. The test zone 2 is therefore arranged prior to the control zone 3 in the direction of a fluid flow.

The test strip device 101 therefore comprises a substrate, disposed on the base support 1 and for clarity purposes indicated by the reference numeral 11. The substrate 11 may be arranged to cover the entire base support 1 or to cover a portion thereof. The substrate 11 is selected such, to enable fast and reproducible migration of liquid sample, such as saliva, in lateral direction (arrow), therefore the substrate 11 is preferably selected from the group consisting of: fiber-, paper- or plastic-based material having porosity and/or a mesh size sufficient for the purposes of the invention. The substrate 11 is further covered with the lamination layer 10. The lamination layer 10 is preferably implemented transparent for proper visualization of test results. Alternatively it may be provided with a number of visualization and/or sample application apertures.

Lamination prevents evaporation of (bio)chemical reagents from the substrate, improves analyte flow rates and provides the test strip device with a sufficient stiffness. Lamination layers may consist of thin polymeric films, such polyethylene terephthalate (PET) -based films, for example. The base support 1 and the lamination layer 10 may be manufactured from the same material such that the substrate 11 is sandwiched between the lamination layers 1 and 10, wherein the lamination layer 1 functions as a base support. It is, however, advantageous, that the base support 1 is produced from the material having a greater stiffness than that utilized for the upper layer 10. Lamination layer 10 may be also utilized for further application of user assistance- and/or guidance marks, in similar manner as disclosed for tape-like material 6 (FIGS. 4A, 4B).

Lamination of the substrate 11 may be realized by any conventional lamination technique. For example, lamination layers 1 and 10 may be fixedly attached to the substrate by means of an adhesive substance (not shown). An adhesive substance may be provided as a separate layer or, alternatively, be pre-applied directly into each lamination layer 1, 10. A so called cold lamination technique may also be utilized. Hot lamination techniques are, however, excluded, since the biological molecules, such as enzymes, efficiently function only within a limited temperature range.

The base support layer 1 may further comprise additional structural elements for facilitating fluid's migration, such as a number of channels/grooves arranged in the direction of a fluid flow, preferably parallel to each other.

The test strip device 101 comprises the test zone 2 and the control zone 3, deposited onto the substrate 11, by the same techniques as disclosed above. Deposition is preferably implemented by printing. Both reactive zones are preferably printed during a single step process, utilizing the same biological ink composition, and therefore contain the same reagents, such as enzymes, chromogenic indicators and/or cofactor(s). The test strip device 101 further comprises a compound buffer 4, such as non-volatile alcohol containing buffer, for example, deposited within a predetermined region between the test zone 2 and the control zone 3. For this embodiment a polyethylene glycol (PEG)—containing buffer is preferably utilized. The lateral fluid migration based solution, embodied herein as 101, provides a compound buffer 4 deposited on the substrate 11 as a separate layer, wherein the deposition thereof is implemented by printing, for example. Therefore, the buffer components are not included into biological ink composition utilized for printing of the reactive zones 2 and 3.

Non-volatile alcohol, such as PEG, disposed between the reactive zones 2 and 3, prohibits an oxidized/reduced, and therefore visible, chromogenic indicator from migrating from the test zone 2 towards the control zone 3, in case liquid sample contains sufficient amount of analyte to trigger the enzymatic colorimetric reaction cascade within the test zone 2. Thus, a required level of reliability is imparted to the embodiment 101.

The test strip device 101 may further contain a supplementary area 12 deposited within a predetermined region subsequent to the control zone 3 in the direction of a fluid flow (arrow, FIGS. 9A, 9B). Layer 12 is intended to improve control indication and comprises compounds enhancing intensity and shades of a control zone indication color. Compounds for the layer 12 include, but are not limited with slowly dissolving polymers PVA or PVP; deposition thereof onto the substrate 11 may be implemented simultaneously with the deposition of the compound buffer 4. In some supplementary embodiment aforesaid PVA and/or PVP may be blended with PEG and utilized within the buffer 4 to enhance visualization at the control zone 3.

The test strip device 101 operates as follows. The liquid sample, such as saliva, is applied onto an appropriately marked end of the device 101. Literal and/or graphical marking is preferably provided on the lamination layer 10. The sample admixes with the reagents comprised within the test zone 2 and, in case of the presence of an analyte of interest, herein alcohol, in sufficient concentration in the sample, causes coloration of the test zone 2. Whether alcohol is absent from the sample or concentration thereof falls below the predetermined indication limit the test zone 2 remains colorless. Liquid sample further advances towards the region, deposited with the alcohol-containing buffer 4, and admixes thereto. Further propagation of the chromogenic indicator in the direction of fluid flow is stopped herein by the non-volatile alcohol-containing buffer. Alcohol-containing buffer-admixed sample further migrates towards the control zone 3, wherein control indication occurs. Since the liquid sample at this stage already contains alcohol, admixed thereto while passing via the alcohol-containing buffer 4, the enzymatic reaction cascade within the control zone 3 is triggered independent on presence or absence of alcohol in the original sample and the control zone is rendered blue, for example. The user may therefore observe visual indications in accordance with the scenarios I and II, depicted on FIG. 1B.

For all the embodiments disclosed thus far visual indication appearing in the control zone 3, confirms the following: a) enzymatic reaction with an analyte proceeded flawlessly; b) substrate worked correctly; c) the user properly performed all the actions required for testing, and sufficient amount of the liquid sample have been applied onto the test strip device; and d) the test strip device is in operating condition, it is not expired and neither of the reagents have evaporated.

Each test strip device implemented in accordance with any embodiment may either be packaged individually into a hermetically sealed package (foil or plastic, for example), or arranged into multipacks containing several test strip devices within the same hermetically sealed package. Hermetical sealing is a necessary precaution to ensure that (bio)chemical components comprised within the test strip device would not evaporate, dry etc.

The different features, elements, element configurations, dimensions, shapes etc. discussed above may be naturally cleverly combined by a skilled person to come up with new variations of same basic embodiments. The invention and its embodiments are thus not limited to the examples described above; instead they may generally vary within the scope of the appended claims.

The present invention may be defined in any of the following numbered paragraphs:

1. A disposable, enzymatic assay based test strip device 100, 100a, 100b, 110, 120, 200, 210, 101 for colorimetric detection of an analyte compound in a body liquid sample, which test strip device comprises at least one reactive test zone 2, 2a, configured to develop a visual indication when the concentration of the analyte compound in the body liquid sample exceeds a predetermined limit, and a reactive control zone 3, configured to develop a visual indication upon being supplied with the body liquid sample, wherein the reactive test zone(s) 2, 2a and the reactive control zone 3 are provided on a substrate material deposited with bio(chemical) reagents; wherein the qualitative composition of the bio(chemical) reagents of the reactive test zone(s) 2, 2a is identical to that of the reactive control zone 3; wherein the test strip device is further provided with a compound buffer 4 comprising at least one chemical compound being a member of the same family as the analyte compound and bearing a characteristic to said family functional group; and wherein the compound buffer 4 is disposed to closely adjoin the reactive control zone 3 such, that the content thereof admixes with the (bio)chemical reagents provided within the reactive control zone 3 upon said reactive control zone 3 is being supplied with the body liquid sample.

2. The test strip device 100, 100a, 100b, 110, 120, 200, 210, 101 of paragraph 1 for the detection of the analyte compound in saliva sample.

3. The test strip device 100, 100a, 100b, 110, 120, 200, 210, 101 of paragraphs 1 and 2 for the detection of an alcohol compound, such as ethanol.

4. The test strip device 100, 100a, 100b, 110, 120, 200, 210, 101 of any of the preceding paragraph, wherein the compound buffer 4 is selected from the group of alcohol compounds, in which the hydroxyl functional group is bound to a carbon atom, preferably from the group of non-volatile alcohol compounds.

5. The test strip device 100, 100a, 100b, 110, 120, 200, 210 of any of the preceding paragraphs, further comprising a base support 1, and in which the reactive control zone 3 and the reactive test zone(s) 2, 2a are provided on individual substrate pads fixedly attached to the base support 1.

6. The test strip device 100, 100a, 100b, 110, 120, 200, 210 of any of the preceding paragraphs, wherein the compound buffer 4 comprises a solid alcohol compound, such polyethylene glycol or polyvinyl alcohol, and forms a film-like layer.

7. The test strip device 100, 100a, 100b, 110, 120, 200, 210 of any of the paragraphs 1-5, wherein the compound buffer 4 comprises a liquid alcohol compound, such glycol, glycerol, ethanol or methanol, solidified by admixing thereof into a solid matrix, such as long-chain polyethylene glycol or acrylate, to form a film-like layer.

8. The test strip device 100, 100a, 100b, 110, 120, 200, 210 of paragraph 5, wherein the compound buffer 4 is disposed within the reactive control zone 3.

9. The test strip device 100, 200 of paragraph 5, further comprising at least one partition element 5, 5a disposed between the reactive zones 2, 2a and 3 such, to prevent bio(chemical) reagents of each reactive zone 2, 2a, 3 from mixing with the bio(chemical) reagents of the neighboring reactive zone(s) and/or with the compound buffer 4.

10. The test strip device 110, 210 of paragraph 5, further comprising a partition element 6, disposed to cover the exposed surfaces of the reactive zones 2, 2a, 3 and to separate said reactive zones from each other, which partition element 6 comprises a number of apertures 7 arranged over each reactive zone 2, 2a, 3 being covered thereby.

11. The test strip device 100, 100a, 100b, 110, 200, 210 of any preceding paragraph, further comprising a layer 9 of predetermined color, disposed between the base support 1 and the reactive zones 2, 2a, 3.

12. The test strip device 120 of any of the paragraphs 5-8, wherein the reactive zone 2 is separated from the reactive zone 3 by means of a slot 8.

13. The test strip device 101 of any of the paragraphs 1-4, wherein the reactive test zone 2 and the reactive control zone 3 are deposited on a common substrate 11, selected from the group consisting of fiber-, paper- or plastic-based mesh materials, which enable capillary forces driven migration of the liquid sample in a lateral direction, wherein the reactive control zone 3 is disposed on the substrate 11 subsequent to the reactive test zone 2 in a direction of fluid flow, and wherein the substrate 11 is disposed on the base support 1 and coated by a lamination layer 10.

14. The test strip device 101 of the paragraph 13, wherein the compound buffer 4 is deposited on the substrate 11 within a predetermined region subsequent to the reactive test zone 2 and prior the reactive control zone 3 in a direction of fluid flow.

15. The test strip device 101 of the paragraph 13, further comprising a supplementary area 12 deposited on the substrate 11 within a predetermined region and spatially arranged subsequent to the reactive control zone 3 in a direction of fluid flow, said supplementary area comprising color intensity and -shade enhancing agents, preserving agents and the like.

16. The test strip device 101 of the paragraphs 14 and 15, wherein the compound buffer 4 and the supplementary area 12 constitute a separate deposition layer, distinct from the one comprising the reactive zones 2 and 3.

17. The test strip device 100, 100a, 100b, 110, 120, 200, 210, 101 of any of the preceding paragraphs, wherein the reactive zones 2, 2a, 3 are provided on a substrate material deposited with a set of bio(chemical) reagents, comprising at least enzymes alcohol oxidase and hydrogen peroxidase and a chromogenic indicator, such as 3,3',5,5'-tetramethylbenzidine.

18. The test strip device 100, 100a, 100b, 110, 120, 200, 210, 101 of any of the paragraphs 1-16, wherein the reactive zones 2, 2a, 3 are provided on a substrate material deposited with a set of bio(chemical) reagents, comprising at least enzymes alcohol dehydrogenase and NAD(P)H—dependent oxidoreductase, a phosphopyridine nucleotide cofactor, such as NAD or NADP and a chromogenic indicator, selected from the group consisting of reazurin and tetrazolium salts.

The invention claimed is:

1. A disposable, enzymatic assay based test strip device for colorimetric detection of an analyte compound in a body liquid sample, comprising:
a base support;
a substrate material disposed on said base support and defining a number of reactive test zones and a reactive control zone; and
a compound buffer comprising a chemical compound same or equivalent to the analyte compound and bearing a functional group characteristic to the analyte compound,
wherein each reactive test zone is configured to develop a visual indication when the concentration of the analyte compound in the body liquid sample exceeds a predetermined limit and the reactive control zone is configured to develop a visual indication upon being supplied with the body liquid sample, wherein the substrate material defining each reactive test zone and the reactive control zone is deposited with a biological ink composition comprising at least one enzyme and a chromogen, said biological ink composition being identical in each reactive test zone and the reactive control test zone; and wherein the substrate material defining the reactive control zone is further disposed with the compound buffer configured to reside within the substrate material defining the reactive control zone such, that the buffer compound is prevented from admixing with the biological ink composition in the reactive control zone until the substrate material, defining said reactive control zone is supplied with the body liquid sample, thereupon the visual indication is developed.

2. The test strip device of claim 1, configured for the detection of an alcohol compound in the body liquid sample.

3. The test strip device of claim 2, configured for the detection of ethanol in the body liquid sample.

4. The test strip device of claim 1, wherein the compound buffer comprises an alcohol compound.

5. The test strip device of claim 1, wherein the compound buffer comprises a mono-, oligo- and/or polysaccharide compound selected from the group of carbohydrate compounds, comprising at least one hydroxyl group bound to carbon backbone.

6. The test strip device of claim 1, in which the reactive control zone and the reactive test zone(s) are each provided on an individual substrate pad fixedly attached to the base support.

7. The test strip device of claim 6, in which the substrate pad defining the reactive control zone contains the biological ink composition and the compound buffer, said biological ink composition and the compound buffer being provided within the substrate material in the form of chemically stable, immiscible substances.

8. The test strip device of claim 6, wherein the compound buffer is provided in the form of a film-like layer disposed in ultimate proximity to the substrate pad defining the reactive control zone, and comprises an alcohol compound-based solid polymer.

9. The test strip device of claim 6, wherein the compound buffer is provided in the form of a film-like layer disposed in ultimate proximity to the substrate pad defining the reactive control zone, and comprises an alcohol compound, selected from the group consisting of: methanol, ethanol, glycol and glycerol, solidified by admixing thereof into the alcohol compound-based solid polymeric matrix.

10. The test strip device of claim 6, further comprising at least one partition element disposed between the reactive zones such, to prevent the biological ink composition of each reactive zone from mixing with the biological ink composition of the neighboring reactive zone(s) and/or with the compound buffer.

11. The test strip device of claim 6, further comprising a partition element in the form of a protective cover, disposed to cover the exposed surfaces of the reactive zones and to separate said reactive zones from each other, which partition element comprises a number of apertures arranged over each reactive zone covered thereby.

12. The test strip device of claim 6, wherein the reactive test zone is separated from the reactive control zone by means of a slot.

13. The test strip device of claim 1, further comprising a layer of a predetermined color, disposed between the base support and the substrate material defining the reactive zones.

14. The test strip device of claim 1, wherein the reactive test zone and the reactive control zone are deposited on a common substrate, selected from the group consisting of fiber-, paper- or plastic-based materials, which enable capillary forces driven migration of the liquid sample in a lateral direction, and wherein the reactive control zone is disposed on the substrate subsequent to the reactive test zone in a direction of fluid flow.

15. The test strip device of claim 14, wherein the compound buffer is deposited on the substrate within a predetermined region subsequent to the reactive test zone and prior the reactive control zone in a direction of fluid flow.

16. The test strip device of claim 1, wherein the substrate material defining each reactive zone is deposited with a biological ink composition, comprising at least enzymes alcohol oxidase and hydrogen peroxidase and a chromogenic indicator.

17. The test strip device of claim 16, wherein the chromogenic indicator is 3,3',5,5'-tetramethylbenzidine.

18. The test strip device of claim 1, wherein the substrate material defining each reactive zone is deposited with a biological ink composition, comprising at least enzymes alcohol dehydrogenase and NAD(P)H—dependent oxidoreductase, a phosphopyridine nucleotide cofactor and a chromogenic indicator, selected from the group consisting of reazurin and tetrazolium salts.

19. The test strip device of claim 18, wherein the phosphopyridine nucleotide cofactor is NAD or NADP.

20. The test strip device of claim 1, further comprising a flavoring agent, disposed into the substrate material, wherein said flavoring agent is a compound or a combination of compounds configured to impart a recognizable flavor and/or taste to the substrate material containing thereof, said flavor and/or taste selected from the group consisting of: citrus, berries, mint, cocoa, caramel, and liquorice.

21. The test strip device of claim 1, further comprising a desiccant, wherein said desiccant is silica gel.

22. The test strip device of claim 1, further comprising at least one lamination layer.

\* \* \* \* \*